(12) United States Patent
Collins et al.

(10) Patent No.: US 8,871,878 B2
(45) Date of Patent: Oct. 28, 2014

(54) ETHYLENE POLYMERIZATION USING DISCRETE NICKEL(II) IMINOPHOSPHONAMIDE COMPLEXES

(71) Applicant: The University of Akron, Akron, OH (US)

(72) Inventors: Scott Collins, North Canton, OH (US); Russell A Stapleton, Raleigh, NC (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 13/667,666

(22) Filed: Nov. 2, 2012

(65) Prior Publication Data

US 2013/0123444 A1  May 16, 2013

Related U.S. Application Data

(63) Continuation of application No. 12/293,187, filed as application No. PCT/US2007/006816 on Mar. 19, 2007, now abandoned.

(60) Provisional application No. 60/784,061, filed on Mar. 17, 2006.

(51) Int. Cl.
*C08F 4/80* (2006.01)
*C08F 4/70* (2006.01)

(52) U.S. Cl.
USPC ........ 526/169.1; 526/169; 526/161; 526/172; 526/115; 526/117; 526/134; 526/170; 526/171; 526/159; 526/164; 526/348; 526/352

(58) Field of Classification Search
USPC ................ 526/172, 161, 169.1, 169
See application file for complete search history.

(56) References Cited

U.S. PATENT DOCUMENTS 5,324,799 A * 6/1994 Yano et al. ............... 526/139
6,268,448 B1 * 7/2001 Collins et al. ............ 526/161

OTHER PUBLICATIONS

Fedotova et al., J. Organomet. Chem., 2004, 689, 3060-3074.*
Boese et al., Z. Anorg. Allg. Chem., 1998, 624, 837-845.*
Stapleton et al., Polymer Preprints, 2004, 45, 93-94.*
Stapleton, R.A. "Bulky Aluminum Scavengers and Nickel Iminophosphonamide Catalysts in Coordination Polymerization of Olefins" Ph.D. Thesis, University of Akron, Apr. 11, 2005.*
Stapleton et al. Organometallics 2006, 25, 2514-2524.*
Schubbe et al. Macromol. Chem. Phys. 1995, 196, 467-478.*

* cited by examiner

*Primary Examiner* — Rip A. Lee
(74) *Attorney, Agent, or Firm* — Renner Kenner Greive Bobak Taylor & Weber

(57) ABSTRACT

The present invention generally relates to a new method of polymerizing ethylene. In one embodiment, the present invention relates to compounds utilized in the polymerization of ethylene and to a synthesis/polymerization method that uses same. In another embodiment, branched polyethylene is synthesized from an ethylene monomer using, in this embodiment, at least one nickel iminophosphonamide ($PN_2$) complex. In still another embodiment, the reaction of (phenyl)(triphenylphosphine)(diphenyl-bis(trimethylsilylimino) phosphorato)-nickel, with Rh(acac) $(C_2H_4)_2$ and ethylene yield a branched polyethylene. In an alternative of this embodiment, the reaction of (phenyl)(triphenylphosphine) (methyl-cis(trimethylsilyl)amino-bis(trimethylsilylimino) phosphorato)-nickel and ethylene, with or without Ni $(COD)_2$, yields a branched polyethylene.

18 Claims, 6 Drawing Sheets

ETHYLENE POLYMERIZATION USING DISCRETE NICKEL(II) IMINOPHOSPHONAMIDE COMPLEXES

CROSS-REFERENCE TO RELATED APPLICATIONS

This application is a continuation of U.S. patent application Ser. No. 12/293,187, filed on Dec. 12, 2008, now abandoned, which is National Stage Entry of PCT/US2007/006816 filed on Mar. 19, 2007, which claims benefit of U.S. Provisional Application No. 60/784,061 filed on Mar. 17, 2006.

FIELD OF THE INVENTION

The present invention generally relates to a new method of polymerizing Ethylene. In one embodiment, the present invention relates to compounds utilized in the polymerization of ethylene and to a synthesis/polymerization method that uses same. In another embodiment, branched polyethylene is synthesized from an ethylene monomer using, in this embodiment, at least one nickel iminophosphonamide ($PN_2$) complex. In still another embodiment, the reaction of (phenyl)(triphenylphosphine)(diphenyl-bis(trimethylsilylimino) phosphorato)-nickel with $Rh(acac)(C_2H_4)_2$ and ethylene yield a branched polyethylene. In an alternative of this embodiment, the reaction of (phenyl)(triphenylphosphine)(methyl-bis(trimethylsilyl)amino-bis(trimethylsilylimino) phosphorato)-nickel and ethylene, with or without $Ni(COD)_2$, yields a branched polyethylene.

BACKGROUND OF THE INVENTION

There is considerable interest in the development of late transition metal complexes as catalysts for the polymerization of olefins. In particular, a variety of cationic and neutral group 10 complexes have proven effective for the production of branched poly(ethylene) from ethylene monomer and it is not necessary to add an α-olefin co-monomer so as to lower density with this general class of catalyst.

Branched poly(ethylene) is produced using these catalyst systems as chain-walking isomerization of the chain, involving a reversible β-H elimination/re-insertion sequence, competes with coordination (trapping) and insertion of monomer. This leads to linear low density polyethylene (LLDPE) with short chain branches or alternately to hyper-branched, amorphous polyethylene (PE) depending on the rates of insertion versus chain-walking.

As has been suggested, PE with long-chain branching as occurs in low density polyethylene (LPDE) or in ethylene-1-octene copolymers produced using Dow Chemicals Insite™ technology and which is desirable from the perspective of melt-processability is generally not available using late metal catalysts.

It is therefore of interest to note that the first preparation of branched PE from ethylene using the ill-defined catalyst reported by Keim et al. is said to provide a material similar to LDPE although no properties are reported. This catalyst formulation is generated in situ in the presence of ethylene through the reaction of either $Ni(COD)_2$ or $(\pi\text{-allyl})_2Ni$ with the sterically hindered phosphorane $(Me_3Si)_2N-P(=NSiMe_3)_2$ (Formula 1). In the case of $(\pi\text{-allyl})_2Ni$ and phosphorane (Formula 1), the product of this reaction in the absence of monomer is shown to be a (π-allyl)Ni-iminophosphonamide ($PN_2$) complex (Formula 2) in (Equation 1). The Pd-analog of (Formula 2) is structurally characterized but is inactive for ethylene polymerization. It is shown here that this complex (Formula 2) is also inactive in ethylene polymerization and thus the structure of the active catalyst in these original formulations is in doubt.

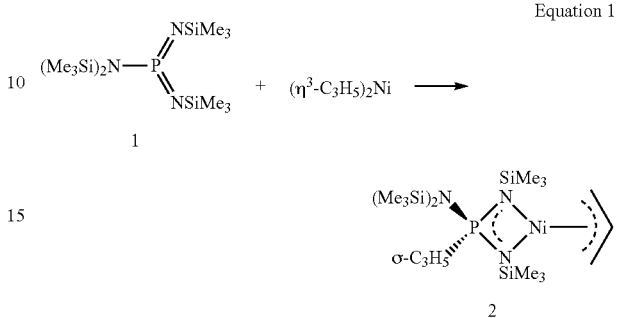

Equation 1

Subsequent work from the group of Yano in Japan established that $Ni(COD)_2$ in combination with phosphorane (Formula 1) could be activated for ethylene polymerization using an α-olefin, and that the polymers contain Me and $H_x^+$ branching in roughly equal amounts as judged from their $^{13}C$ NMR spectra. Branches of intermediate length are not detected in the $^{13}C$ NMR spectra while some of the longer branches present are of sufficient length to influence the hydrodynamic radius of the polymer in solution (i.e., $g'=[\eta]_{br}/[\eta]_{Bn}=0.6$ to 0.7). In a subsequent patent application, Yano et al. demonstrated that the reaction of e.g. $Ni(acac)_2$ with phosphorane (Formula 1) gave rise to an active catalyst formulation in the presence of alkylaluminums, the polymers formed had similar properties.

The poly(ethylene) formed using the Keim family of catalysts is interesting from a materials perspective as it has variable crystallinity depending on both molecular weight and branching but should process similar to low-density PE. However, the activity and stability of these catalyst formulations is too low for practical use.

SUMMARY OF THE INVENTION

The present invention generally relates to a new method of polymerizing Ethylene. In one embodiment, the present invention relates to compounds utilized in the polymerization of ethylene and to a synthesis/polymerization method that uses same. In another embodiment, branched polyethylene is synthesized from an ethylene monomer using, in this embodiment, at least one nickel iminophosphonamide ($PN_2$) complex. In still another embodiment, the reaction of (phenyl)(triphenylphosphine)(diphenyl-bis(trimethylsilylimino) phosphorato)-nickel with $Rh(acac)(C_2H_4)_2$ and ethylene yield a branched polyethylene. In an alternative of this embodiment the reaction of (phenyl)(triphenylphosphine)(methyl-bis(trimethylsilyl)amino-bis(trimethylsilylimino) phosphorato)-nickel and ethylene, with or without $Ni(COD)_2$, yields a branched polyethylene.

In one embodiment, the present invention relates to a method of polymerizing ethylene to form polyethylene, the method comprising the steps of: (a) combining at least one ethylene monomer and at least one nickel catalyst according to the following Formula:

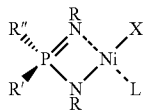

wherein R, R' and R" are independently selected from a $C_1$ to $C_{20}$ alkyl group, a $C_6$ to $C_{10}$ aryl group, a substituted $C_8$ to $C_{10}$ aryl group, and $NR'''$, R''' is independently selected from R', R" or $SiR'_3$, and X is selected from a halogen, a $C_1$ to $C_{20}$ alkyl group, a $C_6$ to $C_{10}$ aryl group, and a substituted version of a $C_6$ to $C_{10}$ aryl group, provided that if X is a halogen and L is absent, the complex is dinuclear with the following structure:

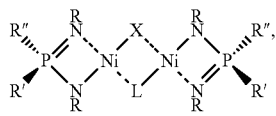

and if L is present, then X is selected from a halogen, a $C_1$ to $C_{20}$ alkyl group, a $C_6$ to $C_{10}$ aryl group, and a substituted $C_6$ to $C_{10}$ aryl group, and L is selected from a tertiary phosphine, or a tertiary amine, nitrile, dialkyl, alkylaryl, diaryl ether, and sulfide; and (b) polymerizing the mixture of Step (a) to yield at least one polyethylene polymer.

In another embodiment the present invention relates to a catalyst for use in the polymerization of ethylene, the composition comprising a compound according to following Formula:

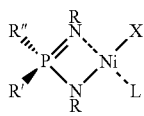

wherein R, R' and R" are independently selected from a $C_1$ to $C_{20}$ alkyl group, a $C_6$ to $C_{10}$ aryl group, a substituted $C_6$ to $C_{10}$ aryl group, and $NR'''_2$, R''' is independently selected from R', R" or $SiR'_3$, and X is selected from a halogen, a $C_1$ to $C_{20}$ alkyl group, a $C_6$ to $C_{10}$ aryl group, and a substituted version of a $C_6$ to $C_{10}$ aryl group, provided that if X is a halogen and L is absent, the complex is dinuclear with the following structure:

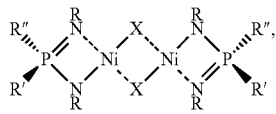

and if L is present, then X is selected from a halogen, a $C_1$ to $C_{20}$ alkyl group, a $C_6$ to $C_{10}$ aryl group, and a substituted $C_6$ to $C_{10}$ aryl group, and L is selected from a tertiary phosphine, or a tertiary amine, nitrile, dialkyl, alkylaryl, diaryl ether, and sulfide.

In still another embodiment the present invention relates to a catalyst for use in the polymerization of ethylene, the composition comprising a compound according to following Formula:

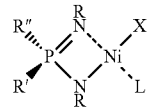

where R, R' and R" are independently selected from a $C_1$ to $C_{20}$ alkyl group, a $C_6$ to $C_{10}$ aryl group, a substituted $C_6$ to $C_{10}$ aryl group, and $NR'''_2$, R''' is independently selected from R', R" or $SiR'_3$, X is selected from a halogen, a $C_1$ to $C_{20}$ alkyl group, a $C_6$ to $C_{10}$ aryl group, and a substituted version of a $C_6$ to $C_{10}$ aryl group, and L is selected from a tertiary phosphine and sulfide.

In yet another embodiment the present invention relates to a method of polymerizing ethylene to form polyethylene, the method comprising the steps of: (i) combining at least one of $Rh(acac)(C_2H_4)_2$ or $Ni(COD)_2$ with at least one nickel catalyst according to the following Formula:

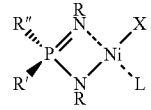

where R, R' and R" are independently selected from a $C_1$ to $C_{20}$ alkyl group, a $C_6$ to $C_{10}$ aryl group, a substituted $C_6$ to $C_{10}$ aryl group, and $NR'''_2$, R''' is independently selected from R', R" or $SiR'_3$, X Is selected from a halogen, a $C_1$ to $C_{20}$ allyl group, a $C_6$ to $C_{10}$ aryl group, and a substituted version of a $C_6$ to $C_{10}$ aryl group, and L is selected from a tertiary phosphine and sulfide, (ii) adding at least one ethylene monomer the mixture formed in Step (i); and (iii) polymerizing the mixture of Step (ii) to yield at least one polyethylene polymer.

In another embodiment the present invention relates to a method for preparing a nickel catalyst according to the following Formula:

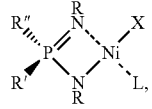

the method comprising the steps of: (A) reacting an alkali metal salt or a derivative of a $R"(R')P(=NR)NHR$ compound with R', R" and R and a suitable Ni(II) halide salt or complex $L_2NiX(Y)$ wherein Y is a halogen, and wherein R, R' and R" are independently selected from a $C_1$ to $C_{20}$ alkyl group, a $C_6$ to $C_{10}$ aryl group, a substituted $C_6$ to $C_{10}$ aryl group, and $NR'''_2$, R''' is independently selected from R', R" or $SiR'_3$, X is selected from a halogen, a $C_1$ to $C_{20}$ alkyl group, a $C_6$ to $C_{10}$ aryl group, and a substituted version of a $C_6$ to $C_{10}$ aryl group, and L is selected from a tertiary phosphine, or a tertiary amine, nitrile, dialkyl, alkylaryl, diaryl ether, and sulfide to yield at least one nickel catalyst; and (B) collecting the at least one nickel catalyst for use in the polymerization of ethylene.

In another embodiment the present invention relates to a method for preparing a nickel catalyst according to the following Formula:

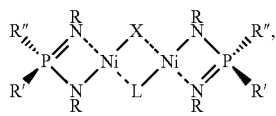

the method comprising the steps of: (I) reacting an alkali metal salt or a derivative of a R"(R')P(=NR)NHR compound with R', R" and R and a Ni(II) halide salt or complex $L_2NiX_2$ wherein X is a halogen, wherein R, R' and R" are independently selected from a $C_1$ to $C_{20}$ alkyl group, a $C_6$ to $C_{10}$ aryl group, a substituted $C_6$ to $C_{10}$ aryl group, and $NR'''_2$, R''' is independently selected from R', R" or $SiR'_3$, and (II) collecting the at least one nickel catalyst for use in the polymerization of ethylene.

In another embodiment the present invention relates to a method for preparing a nickel catalyst according to the following Formula:

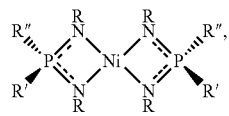

the method comprising the steps of: (1) reacting an alkali metal salt or a derivative of an alkali metal salt or similar derivative of a R"(R')P(=NR)NHR compound with R', R", R, and a Ni(II) halide salt or complex $L_2NiY_2$, wherein Y is a halogen, wherein R, R' and R" are independently selected from a $C_1$ to $C_{20}$ alkyl group, a $C_6$ to $C_{10}$ aryl group, a substituted $C_6$ to $C_{10}$ aryl group, and $NR'''_2$, R''' is independently selected from R', R" or $SiR'_3$; and (2) collecting the at least one nickel catalyst for use in the polymerization of ethylene.

In another embodiment the present invention relates to a catalyst for use in the polymerization of ethylene, the composition comprising a compound according to following Formula:

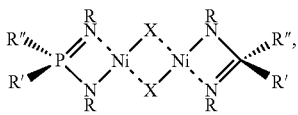

wherein X is a halogen, wherein R, R' and R" are independently selected from a $C_1$ to $C_{20}$ alkyl group, a $C_6$ to $C_{10}$ aryl group, a substituted $C_6$ to $C_{10}$ aryl group, and $NR'''_2$, and wherein R''' is independently selected from R', R" or $SiR'_3$.

In yet another embodiment the present invention relates to a catalyst for use in the polymerization of ethylene, the composition comprising a compound according to following Formula:

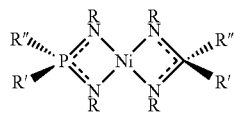

wherein Y is a halogen, wherein R, R' and R" are independently selected from a $C_1$ to $C_{20}$ alkyl group, a $C_6$ to $C_{10}$ aryl group, a substituted $C_6$ to $C_{10}$ aryl group, and wherein $NR'''_2$, R''' is independently selected from R', R" or $SiR'_3$.

DETAILED DESCRIPTION OF THE INVENTION

Figure 1:
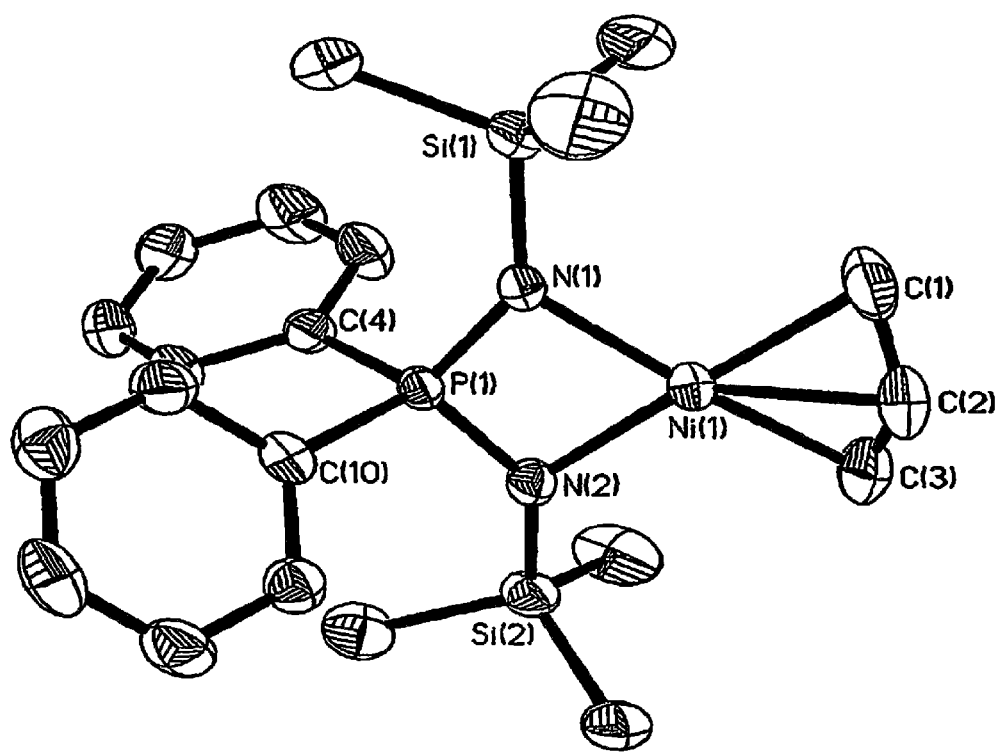
FIG. 1 details the molecular structure of the Formula 2c, and is illustrated herein with 50% thermal ellipsoids and with hydrogen atoms omitted.
Figure 2:
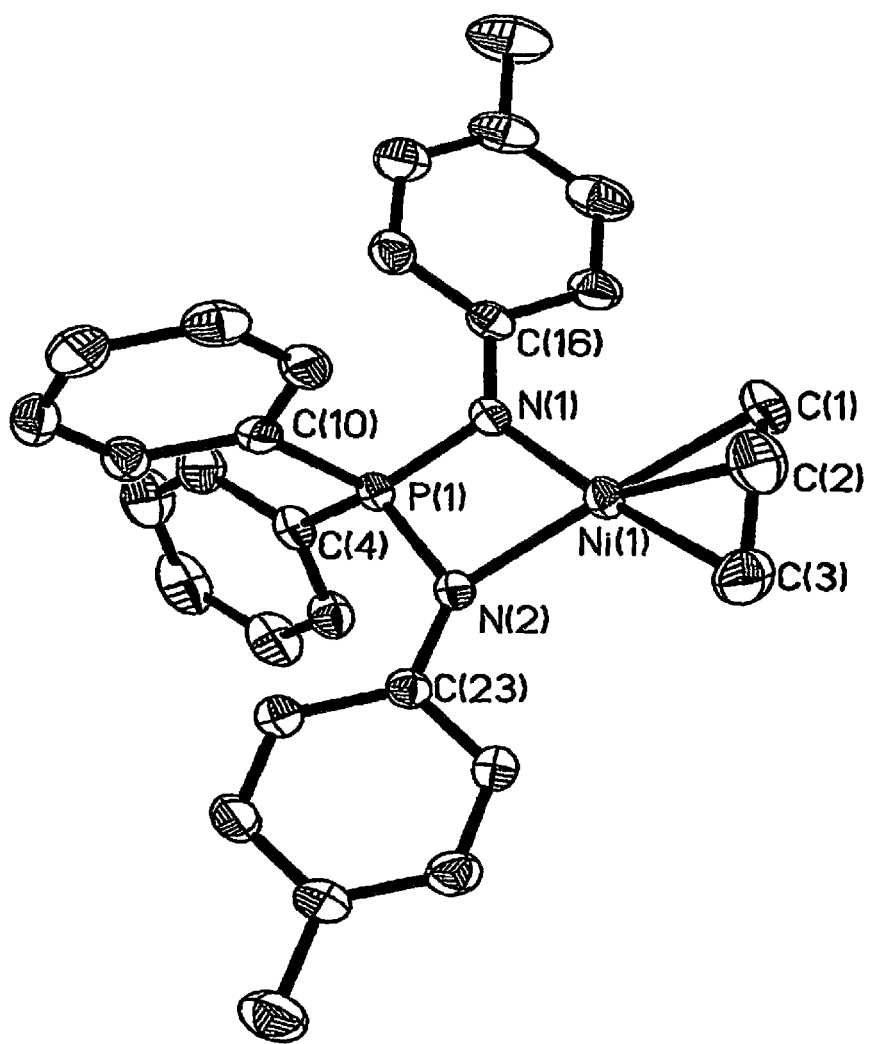
FIG. 2 details the molecular structure of the Formula 2d, and is illustrated herein with 50% thermal ellipsoids and with hydrogen atoms omitted.
Figure 3:
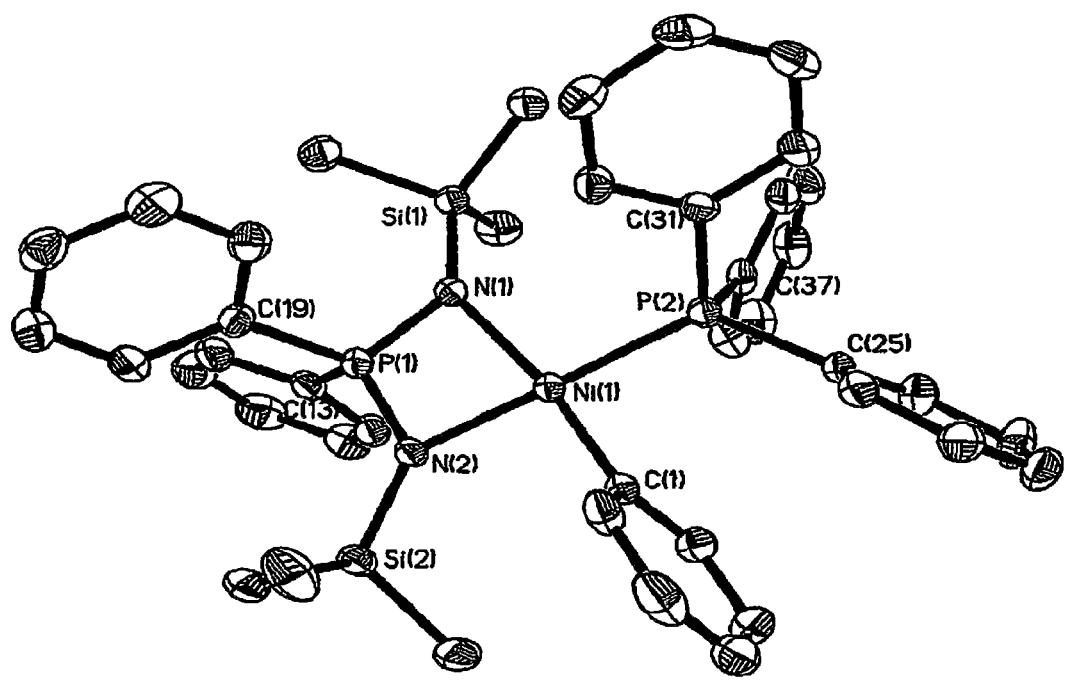
FIG. 3 details the molecular structure of the Formula 5, and is illustrated herein with 30% thermal ellipsoids and with hydrogen atoms omitted.
Figure 4:
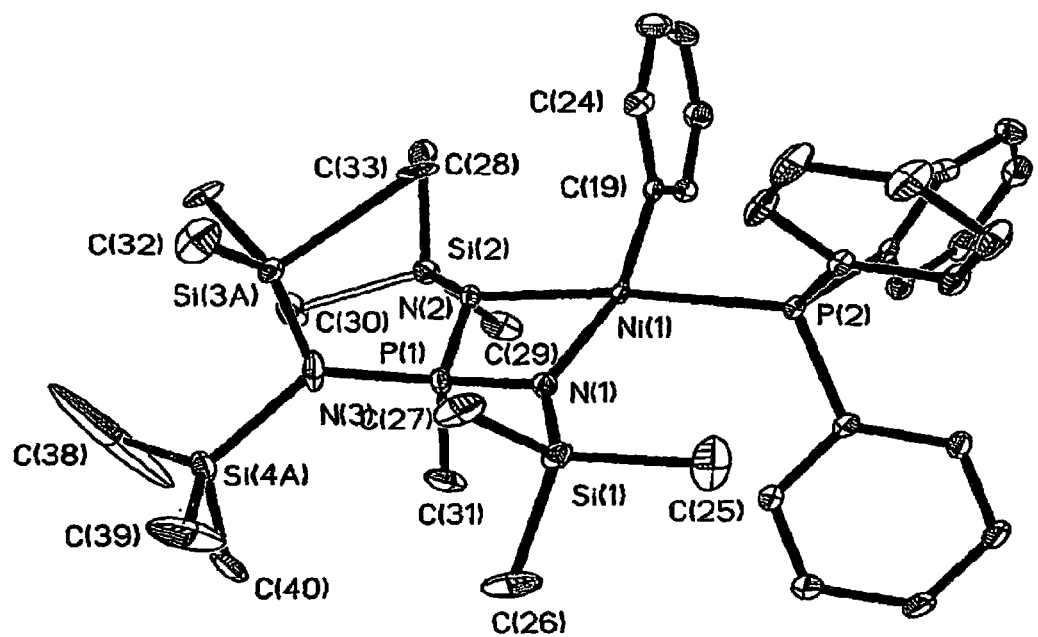
FIG. 4 details the molecular structure of Formula 6, and is illustrated herein with 30% thermal ellipsoids and H-atoms omitted for clarity.

The present invention generally relates to a new method of polymerizing ethylene in one embodiment, the present invention relates to compounds utilized in the polymerization of ethylene and to a synthesis/polymerization method that uses same. In another embodiment branched polyethylene is synthesized from an ethylene monomer using, in this embodiment, at least one nickel iminophosphonamide ($PN_2$) complex. In still another embodiment, the reaction of (phenyl)(triphenylphosphine)(diphenyl-bis(trimethylsilylimino) phosphorato)-nickel with $Rh(acac)(C_2H_4)_2$ and ethylene yield a branched polyethylene. In an alternative of this embodiment, the reaction of (phenyl)(triphenylphosphine) (methyl-bis(trimethylsilyl)amino-bis(trimethylsilylimino) phosphorato)-nickel and ethylene, with or without Ni $(COD)_2$, yields a branched polyethylene.

The syntheses and structures of discrete (π-allyl)nickel iminophosphonamide ($PN_2$) complexes (Formulas 2a to 2d) from the reaction of (π-allyl)nickelbromide and the corresponding $PN_2$ ligands (Formulas 3a to 3bb), or from the reaction of (π-allyl)$_2$Ni and phosphorane (Formula 1) are disclosed. Purified complexes (Formulas 2a to 2d) are not active for ethylene polymerization; it is only when phosphorane (Formula 1) and Ni(π-allyl)$_2$ are combined in situ in the presence of monomer that high molecular weight, branched poly(ethylene) is formed as reported by Keim et al. As also reported by Keim et al. (and subsequently confirmed by Yano et al.) branched PE can also be prepared from phosphorane (Formula 1) and $Ni(COD)_2$. Both methods are exemplified herein.

A $PN_2NiPh(PPh_3)$ complex (Formula 5) is prepared from $NiPh(PPh_3)_2Br$ and $PN_2$ ligand (Formula 3a) and is structurally characterized Formula 5 is shown to be effective in the polymerization or oligomerization of ethylene under a variety of conditions. The reactions of Formula 5 with various phosphine scavengers are observed and of these only Rh(acac)(C$_2$H$_4$)$_2$ is both effective and selective for PPh$_3$. Hard Lewis acids, including AlMe$_3$, B(C$_6$F$_5$)$_3$ and PMAO, have a pronounced tendency towards abstraction of the PN$_2$ or other anionic ligands in these unhindered complexes. All of the complexes discussed herein are extremely active for ethylene dimerization in the presence of PMAO. In the presence of stoichiometric Rh(I), Formula 5 in the presence of ethylene produces branched PE oligomers at a modest activity level. A more sterically hindered compound, Formula 6, is prepared that yields higher molecular weight branched PE. PE is confirmed to have the same structure as PE produced using the catalyst formulations disclosed by Keim et al. (Keim; Appel; Storeck; Krueger; Goddard. New nickel and palladium complexes with aminobis(imino)phosphoarane ligands in the polymerization of ethylene. Angewandte Chemie (1981), 93 (1), 91-2.) and Yano et al (Yano; Hasegawa, Yamada. Ethylene polymerization with a nickel-aminobis(imino)phosphorane catalyst in the presence of another olefin. Kobunshi Ronbunshu (2002), 59 (6) 377-381). In this embodiment, it is unnecessary to use a phosphine scavenger although Formula 6 is more active in the presence of excess Ni(COD)$_2$.

Figure 6:
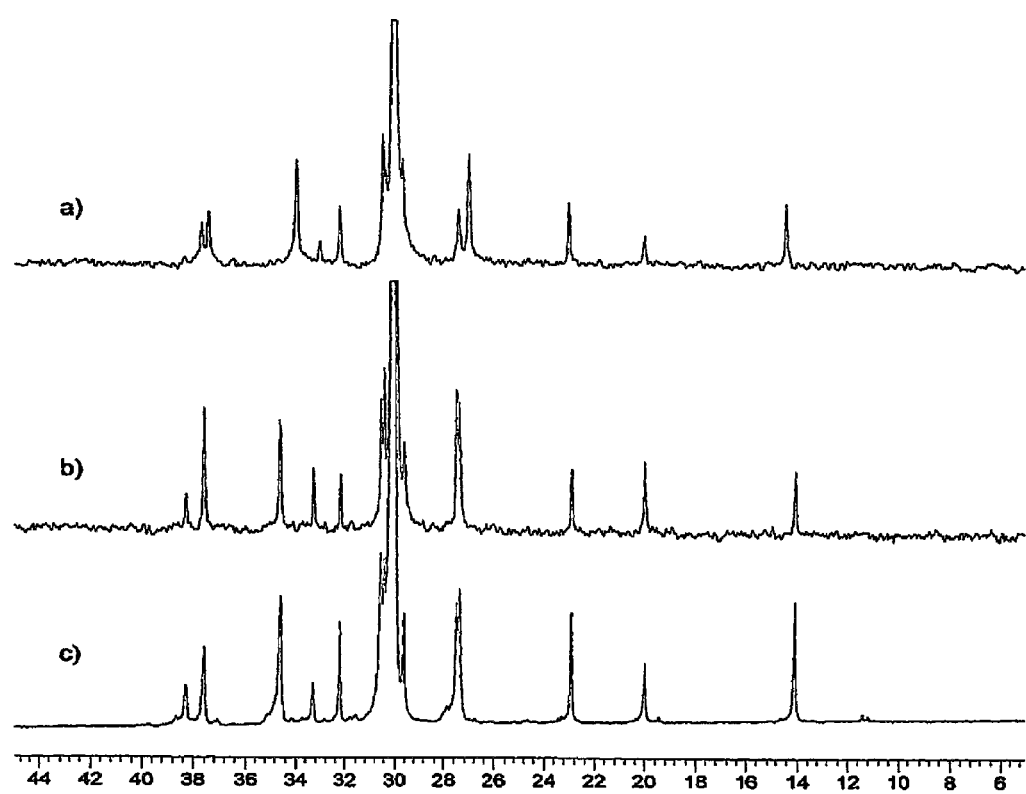
FIG. 6 is a number spectrum detailing the $^{13}C$ NMR spectra of branched PE produced using: (a) $(TMS)_2N(Me)P(NTMS)_2 NiPh(PPh_3)$, Formula 6, (75 MHz, $CDCl_3$); (b) phosphorane, Formula 1, and $Ni(\eta^3$-allyl$)_2$—Comparative Example 1 (100 MHZ, o-DCB-$d_4$, 120° C.); and (c) phosphorane, Formula 1, and $Ni(COD)_2$—Comparative Example 2 (187 MHz, o-DCB-$d_4$, 120° C.).

When pure, none of these π-allyl compounds, Formulas 2a to 2d, are active for ethylene polymerization under a variety of conditions of temperature and pressure as reported by Keim et al. Instead, high molecular weight (M$_w$ approximately 10$^5$ to 10$^6$ with PDI approximately 2 to 3 based on SEC-MALLS) poly(ethylene) (T$_m$=98° C.) is produced, albeit at low activity (approximately 10$^3$ grams PE/mol Ni×h), only when phosphorane Formula 1 and (π-allyl)$_2$Ni are combined in a reactor previously saturated with ethylene at 450 psig and 25° C. The material is branched (about 30-40 total branches/1000 carbon atoms) and with a microstructure consistent with that reported by Yano et al. In addition, lower molecular weight PE with a similar structure can be prepared using a phosphorane compound, Formula 1, and Ni(COD)$_2$, optimally in the presence of an α-olefin, via a method detailed by Yano et al. The $^{13}$C NMR spectra of these materials are depicted in FIGS. 6b and 6c where the branches are either 1 or ≥6 C atoms in length. The latter are usually referred to as long-chain branches and analyses of these polymers by either solution viscosity or SEC-light scattering confirm the presence of long-chain branches.

Synthesis, Structure and Chemistry of a PN2Ni((PPh3)Ph-Complex:

Mono- and bis-PN$_2$ complexes of Ni have been previously reported. Both were formed in low yield from the reaction of sterically hindered PN$_2$ salts and Ni-halides in ethereal solution. Using Li- or K-salt of ligand, Formula 3a, this reaction proceeds in higher yield and generally affords the deep blue and paramagnetic bis(PN$_2$) compound, Formula 4, as the sole product, regardless of stoichiometry or mode of addition (see Equation 4). The same result is observed when using trans-NiCl$_2$(PPh$_3$)$_2$ as a reagent, suggesting the intermediate mono-PN$_2$Ni(L)Cl complex must be more reactive towards further substitution than the starting material.

Equation 2

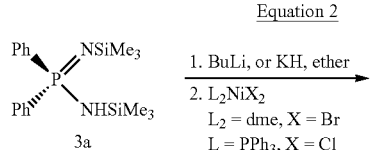

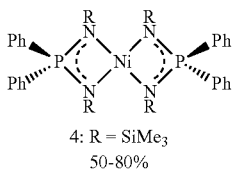

4: R = SiMe$_3$
50-80% in view of this, the use of a pre-formed L$_2$NiR(X) is investigated, and metathetical reaction of (Ph$_3$P)$_2$NiPh(Br) with the K-salt of ligand (Formula 3a) proceeded in high yield to furnish the expected PN$_2$ compound, Formula 5 (see Equation 5).

Equation 3

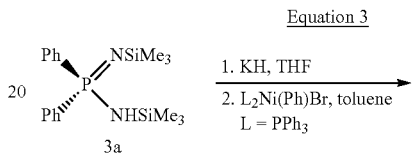

5: R = SiMe$_3$
80%

Figure 5:
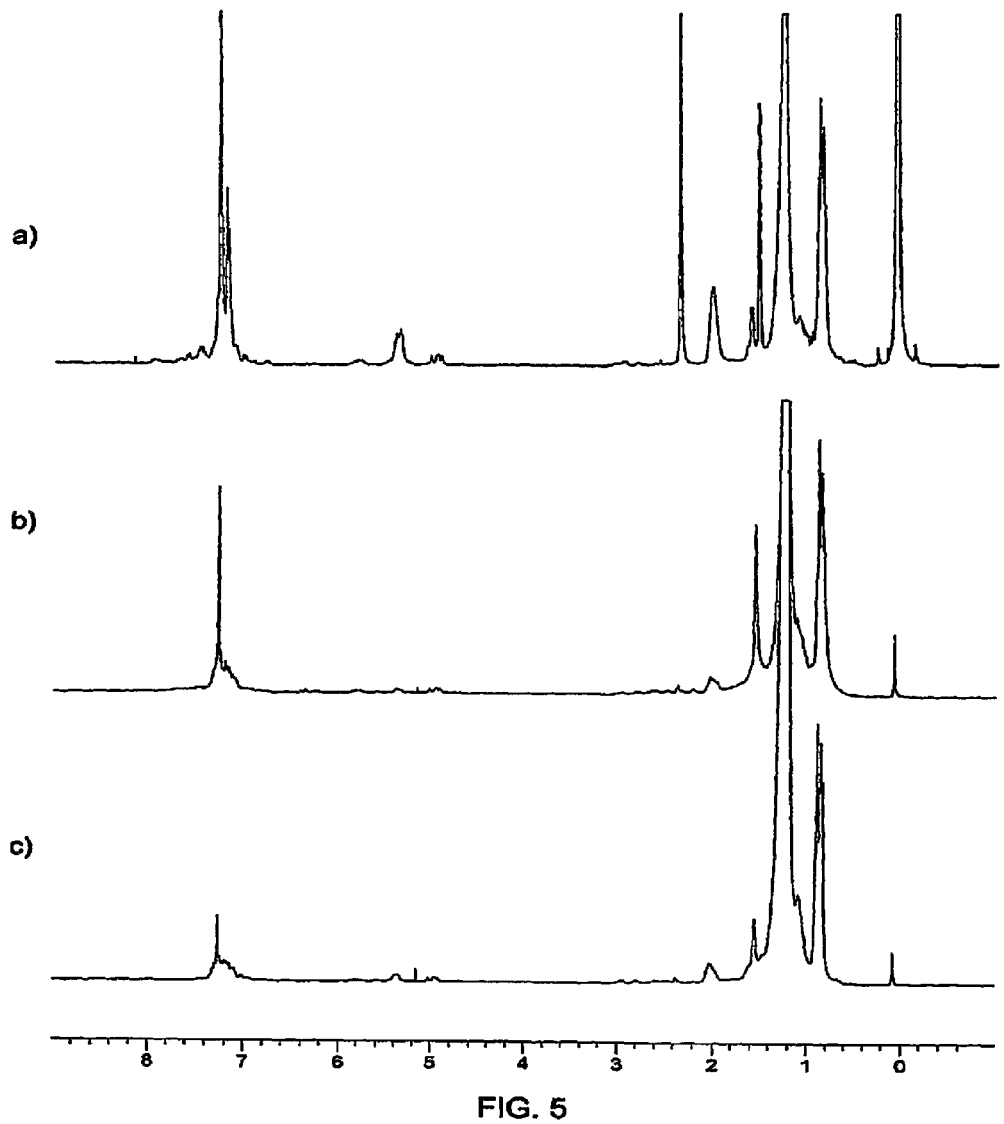
FIG. 5 is a number of spectrum detailing: (a) the $^1H$ NMR spectra (300 MHz, $C_6D_6$) of ethylene oligomers prepared using Formula 5 (2.0 mM) and $Rh(acac)(C_2H_4)_2$ (1.0 mM) at 25° C. and 150 psig $C_2H_4$; (b) $^1H$ NMR spectra of higher molecular weight PE prepared using $(TMS)_2N(Me)P(NTMS)_2NiPh(PPh_3)$, Formula 6, in the presence of $Ni(COD)_2$, and (c) $^1H$ NMR spectra of higher molecular weight PE prepared using $(TMS)_2N(Me)P(NTMS)_2NiPh(PPh_3)$, Formula 6.

The compound of Formula 5 is Inactive for ethylene polymerization in the absence of a phosphine scavenger. Only Rh(I) appears selective (and effective) for phosphine abstraction. In the presence of stoichiometric Rh(acac)(C$_2$H$_4$)$_2$, at 25° C. and 150 psig, the C$_2$H$_4$ compound containing, Formula 5, (2 mM) slowly oligomerized ethylene (A approximately 10$^2$-10$^3$ g PE/mol Ni×h) to form a branched material where the $^1$H NMR spectrum of this material (see FIG. 5) reveals signals due to terminal vinyl and internal vinylene protons, and enhanced intensity for terminal Me groups. By comparing the integrated intensities of these signals to those of the main chain protons, it is determined that M$_n$=530 (X$_n$=19) with a branching frequency corresponding to 80 methyl groups/1000 carbon atoms (or approximately 3 methyl groups per chain in this case).

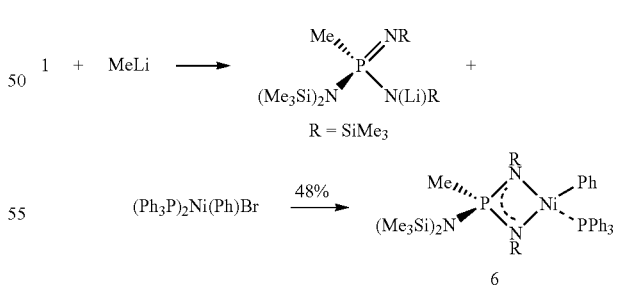

A more sterically hindered version of this type of complex is prepared in a similar manner (see Equation 3) and unlike its less sterically hindered analog, this complex is active for ethylene polymerization in the absence of a phosphine scavenger though it's activity improves by a factor of 20 in the presence of an excess of Ni(COD)$_2$. As shown in FIG. 5(b), the branched PE formed is of much higher molecular weight as the unsaturated end-groups are not readily detectable. Further as shown in FIG. 6(a) the structure and even the relatively intensity of the branches formed are essentially identical to those observed in PE prepared using the ill-defined catalyst formulations reported previously.

Although compounds of the present invention provide branched PE from ethylene either by themselves or on activation with a selective phosphine scavenger, they can also be activated for ethylene oligomerization using an excess methylaluminoxane (PMAO) or a stoichiometric amount $B(C_6F_5)_3$. Formulas 2a to 2d, Formula 4 and especially Formula 5 are all active catalysts for ethylene dimerization with activities of $10^6$ to $10^7$ g $C_2H_4$/mol Ni×h at 150 psig $C_2H_4$ and 200:1 Al:Ni at 25° C. There is no evidence for formation of any high molecular weight material in these reactions (branched or otherwise), and the selectivity for butene (1- and cis/trans-2-butene) generally exceeds 90% FIG. 7 depicts a gas chomatograph trace of the mixture formed from Formula 5, ethylene and PMAO.

Cyclic Embodiments

In another embodiment of the present invention, the Rs as shown in formulas above can together comprise a macro-cyclic or macro-bicyclic ring with rings located above and below the plane defined by P, Ni and the two N atoms as suggested by the following formula:

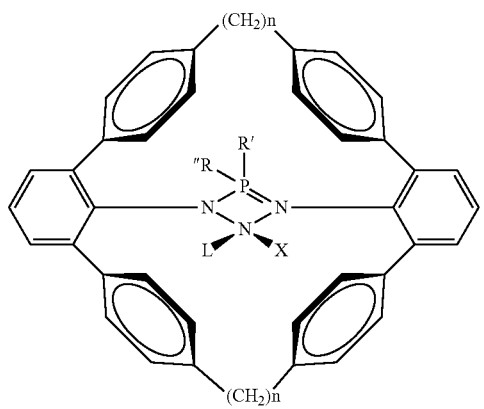

(7)

This kind of structural feature is found in other Ni catalysts and is known to confer enhanced thermal stability to the resulting catalyst as well as providing other attractive features such as quasi-living polymerization behavior at elevated temperature.

In still yet another embodiment of the current invention, R' and R" may be joined together to form a cyclic structure as is shown in the following examples, which are illustrative examples and are not meant to be comprehensive:

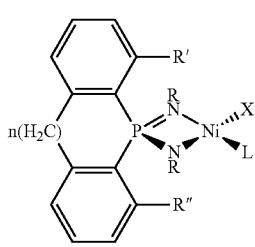

(8)

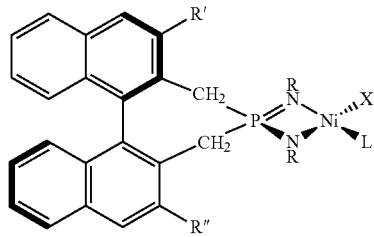

(9)

In the above structures, the complex can be chiral due to the torsional asymmetry associated with the P-containing, heterocyclic ring. Chiral complexes are of interest in connection with the stereoregular polymerization of α-olefins to form tactic polymers; however, this has not proven possible with other late-metal catalysts at conventional polymerization temperatures, in part because of the unavailability of suitable, stereorigid ligands.

EXAMPLES

All materials are obtained from Aldrich Chemical Co. or Strem Cherm Co. Ltd., and purified as required, unless otherwise noted. All synthetic procedures are conducted under a $N_2$ atmosphere using Schlenk techniques or in a MBraun MB-150 glove-box. Tetrahydrofuran, diethyl ether, toluene, hexane and dichloromethane are purified by passage through activated La Roche A-2 alumina and Engelhard CU-0226s Q-5 columns.

Routine $^1H$, $^{19}F$ and $^{13}C$ NMR spectra are recorded on a Varian Mercury or Gemini 300 MHz instrument. Tetrahydrofuran-$d_8$ is dried over molecular sieves. Benzene-$d_6$, toluene-$d_8$, and bromobenzene-$d_5$ are distilled from Na or Na/K alloy prior to use. Acetonitrile-$d_3$, methylene chloride-$d_2$, and chloroform-$d_1$ are distilled from $P_2O_5$ and stored over 4 Angstroms mole sieves. $^1H$ NMR spectra are referenced with respect to residual protonated solvent, while $^{13}C$ NMR spectra are referenced with respect to deuterated solvent $^{19}F$ NMR spectra are referenced with respect to tetrafluoro-p-xylene (TFX: δ-145.69 in toluene-$d_8$), $^{31}P$ NMR spectra are referenced to a phosphoric acid external standard. Variable temperature experiments are performed using Varian Inova 400 MHz instrument. The spectrometer thermocouple is calibrated to within 5% of actual temperature using a sample of MeOH. IR spectra are obtained on a Digilab Excalibur FTS 3000 spectrometer. Elemental analyses are performed either by Oneida Research Services or Galbraith Laboratories.

Tris(perfluorophenyl)borane is pre-dried in a hexane solution containing activated molecular sieves 4 Angstroms, and recrystallized from hexane at −30° C. The compounds Ni(COD)$_2$, (η$^3$-C$_3$H$_5$)$_2$Ni [η$^3$-(2-Me)C$_3$H$_4$]$_2$Ni, [(η$^3$-C$_3$H$_5$)NiBr]$_2$, [(Me$_3$Si)$_2$N—P(=NSiMe$_3$)$_2$] (Equation 1), [Ph$_2$P(NHTol)(=NTol)] (Formula 3b), and (PPh$_3$)$_2$Ni(Ph)Br, are prepared according to procedures known to those of skill in the art.

N,N'-Bis(trimethylsilyl)-(diphenyl)iminophosphonamide (Formula 3a)

Ph$_2$P(NHTMS)(=NTMS) is prepared using a modified literature preparation. Diphenylphosphine (6.6 grams, 30 mmol) is dissolved onto 75 mL of hexane. Trimethylsilyiazide (8 grams, 72 mmol) is added and the solution heated under reflux for 12 hours. The solution is pumped to dryness and the product distilled at 60 to 100° C. at 0.001 mmHg. The product (11.4 grams, 90%) is a clear colorless liquid. $^1$H NMR (300 MHz, benzene-$d_6$, 298 K): δ 0.19 (s, 9H, NBSi—CH$_3$), 0.36 (s, 9H, NSi—CH$_3$), 1.88 (bs, 1H, NH), 7.04-7.10 (m, 6H, p/m-Ar), 7.67-7.75 (m, 4H, o-Ar). $^{31}$P MMR (121.4 MHz, benzene-$d_6$, 298 K): δ 0.70.

[Potassium][N,N'-Bis(trimethylsilyl)-diphenyl)iminophosphonamide]

The potassium salt of (Formula 3a) is prepared by stirring KH (1.4 grams, 35 mmol) into 25 ml of THF and then (Formula 3a) (6.0 grams, 16.6 mmol) is dropped in slowly and stirred for 1 hour. One note of caution is made regarding the need to add (Formula 3a) slowly to prevent rapid H$_2$ formation. The resulting solution is filtered through Celite and dried under vacuum. The product is recrystallized from toluene (8 ml) layered with hexane (20 ml). The [K][Ph$_2$P(NTMS)$_2$] forms colorless crystals (4.92 g, 75%) More material could be isolated from the supernatant. $^1$H NMR (300 MHz, benzene-$d_6$, 298 K): δ 0.06 (s, 18H, Si—CH$_3$), 7.78 (m, 4H, o-Ar), 7.20 (m, 6H, p/m-Ar). $^{31}$P NMR (121.4 MHz, benzene-$d_6$, 28 K): δ 5.67. This material is used directly for the preparation of Formula 5.

($\eta^3$-Allyl)(σ-allyl-[Bis(trimethylsilyl)amino]-bis(trimethylsilylimino)phosphorato)nickel (Formulas 2a to 2b)

A modified procedure, based on that reported by Keim, is used to prepare Formulas 2a to 2b. Formula 1 (1.00 grams, 2.73 mmol) is dissolved into 4.5 mL of hexane. In a separate flask 1 equivalent of ($\eta^3$-C$_3$H$_5$)$_2$Ni is dissolved into 4.5 mL of hexane. The two solutions are mixed to form a deep red solution, which upon evacuation at 0.01 mmHg yields an orange powder (1.5 grams, 95%) of Formulas 2a to 2b. $^1$H and $^{31}$P NMR spectra agree with those reported in the literature. Deep red crystals are grown from evaporation of a hexane solution. $^1$H NMR (300 MHz, benzene-$d_6$, 298 K): major isomer: δ 0.21 (s, 18H, NSiCH$_3$), 0.52 (s, 18H, N(SiCH$_3$)$_2$), 1.49 (dd, J=12.7 Hz, 2H, anti-⅓-allyl-CH$_2$), 2.51 (ddt, J=14.3, 6.6, 1.7 Hz, 2H, P—CH$_2$), 2.81 (dd, J=12.7 Hz, 2H, syn-⅓-allyl-CH$_2$). 5.05-4.85 (tt, J=6.7, 12.7 Hz, 1H, allyl-CH), 5.05-4.85 (dt, 1H, P-allyl-cis-CH$_2$), 5.24-5.16 (dt, 1H, P-allyl-trans-CH$_2$), 6.13 (m, 1H, P-allyl-CH) minor isomer: δ 0.22 (s, 18H, NSiCH$_3$), 0.40 (s, 18H, N(SiCH$_3$)$_2$), 1.59 (dd, J=12.7 Hz, 2H, anti-⅓-allyl-CH$_2$), 2.72 (ddt, J=14.3, 7.0, 1.3 Hz., 2H; P—CH$_2$), 2.78 (dd, J=7.0 Hz, 2H, syn-⅓-allyl-CH$_2$), 5.05-4.85 (m, 1H, allyl-CH), 5.24-5.16 (dt, 1H, P-allyl-cis-CH$_2$), 5.34 (dt, 1H, P-allyl-trans-CH$_2$), 6.71 (m, 1H, P-allyl-CH). $^{31}$P NMR (121.4 MHz, benzene-$d_6$, 298 K): major isomer δ 34.26 (s, 1P, P), minor isomer 33.25 (s, 1P, P). By integration of the $^{31}$P spectrum, the ratio of major to minor isomer is 1.5:1.

(η3-Allyl) (Diphenyl-bis(trimethylsilylimino)phosphorato)nickel (Formula 2c)

Ligand (Formula 3a) (708 mg, 1.97 mmol) in 10 mL of THF is cooled to −80° C. and 1 equivalent of "BuLi in hexanes (2.62 M, 0.752 mL, 1.97 mmol) is added by syringe. This solution is allowed to warm to 20 C. In a separate flask [(η3-C$_3$H$_5$)NiBr]$_2$ (353 mg, 0.982 mmol) is dissolved into 10 mL of THF. The ligand solution is cooled to −80° C., and the [(η$^3$-C$_3$H$_5$)NiBr]$_2$ solution is added via canula. The resulting red solution is pumped to dryness and dissolved in hexane. The product is filtered through Celite and crystallized by slow evaporation to yield dark red crystals (720 mg, 80%). $^1$H NMR (300 MHz, benzene-$d_6$, 298 K): δ 0.04 (s, 18H, SiCH$_3$), 1.67 (dd, J=12.9 Hz, 2H, anti-⅓-allyl-CH$_2$), 2.86 (dd J=7.5 Hz, 2H, syn-⅓-allyl-CH$_2$), 5.01 (tt, J=6.0 Hz, 1H, allyl-CH), 7.04 (m, 3H, p/m-Ar), 7.12 (m, 3H, p/m-Ar), 7.79 (m, 2H, o-Ar), 8.06 (m, 2H, o-Ar). $^{31}$P NMR (121.4 MHz, benzene-$d_6$, 298 K): δ 40.1. IR (KBr, cm-1): 2948 (m), 2892 (sh), 2360 (m), 2341 (sh), 1587 (w), 1498 (m), 1481 (sh), 1434 (s), 1398 (sh), 1245 (s), 1139 (s), 1101 (sh), 854 (s), 831 (sh), 520 (m). As calculated for C$_{21}$H$_{33}$N$_2$NiPSi$_2$: C, 54.91; H, 7.24. Found C, 54.62; H, 7.14.

A red crystal of Formula 5 with dimensions 0.33×0.23×0.22 mm is coated in PEK and mounted on a glass fiber, which is placed under a stream of nitrogen on the goniometer head of a Bruker Apex CCD diffractometer. The full sphere of data is collected to 28.28° (θ) using graphite-monochromated MoK-α radiation (λ=0.71073 Angstroms) at 180 K. The reflections are collected using ω scans. Unit cell dimensions are based on data collected using SMART and indexed using the SAINT algorithm. The total number of reflections collected is 6014 between 1.73° to 28.8° in θ. Structure solution, refinement and modeling are accomplished using the Bruker SHELXTL package. The structure is solved toy Patterson and Fourier methods and refined by full-matrix least-squares refinement on F$^2$. Allylic hydrogen atoms are found and refined from a Fourier difference map. The remaining hydrogens are fitted with a riding model. The final cycles of refinement converged with R=0.0488 and R$_w$=0.0871.

(η$^3$-Allyl)(Diphenyl-bis(4-methyl-phenyl)phosphorato)nickel (Formula 2d)

Ligand (Formula 3b) (100 grams, 2.31 mmol) in 10 ml of THF is cooled to −80° C. and 2 equivalents of "BuLi in hexanes (1.85 M, 2.49 mL, 4.62 mmol) is added by syringe. This solution is allowed to warm to 20° C. In a separate flask [(η$^3$-C$_3$H$_5$)NiBr]$_2$ (539 mg, 1.15 mmol) is dissolved into 10 ml of THF. The ligand solution is cooled to −80° C., and the [(η$^3$-C$_3$H$_5$)NiBr]$_2$ solution added via canula. The resulting red solution is pumped to dryness and dissolved in toluene. The product is filtered through Celite and the solvent evaporated. Compound 2d is isolated as red crystals (842 mg, 74%) by crystallization from CH$_2$Cl$_2$ at −30° C. $^1$H NMR (300 MHz, benzene-$d_6$, 298 K): δ 1.94 (dd, J=13.2 Hz, 2H, anti-⅓-allyl-CH$_2$), 2.07 (s, 6H, ArCH$_3$), 2.92 (dd, J=7.9 Hz, 2H, syn-⅓-allyl-CH$_2$), 5.26 (tt, J=6.5 Hz, 1H, allyl-CH), 6.82 (m, 6H, o/m-ArCH$_3$), 7.00 (m, 6H, p/m-Ar), 7.91 (m, 2H, o-Ar). 8.10 (m, 2H, o-Ar), $^{31}$P NMR (121.4 MHz, benzene-$d_6$, 298 K): δ 41.7, IR (KBr, cm$^{-1}$); 3019 (w): 2913 (w), 1806 is), 1504 (s), 1434 (sh), 1286 (s), 1267 (sh), 1176 (m), 1105 (s), 997 (s), 908 (m), 815 (s), 688 (s), 597 (m), 507 (s). As calculated for C$_{29}$H$_3$N$_2$NiP: C, 69.78; H, 6.66. Found: C. 70.04; H, 5.99.

A red crystal of Formula 2d with dimensions 0.37×0.34×0.31 mm is coated in PEK and mounted on a glass fiber which is placed under a stream of nitrogen on the goniometer head of a Bruker Apex CCD diffractometer. The full sphere of data is collected to 30.30° (θ) using graphite-monochromated MoK-αradiation (λ=0.71073 Angstroms) at 180 K. The reflections are collected using ω scans. Unit cell is collected in SMART and indexed in SAINT. The total number of reflections collected is 7207 between 1.50°-28.8° (θ). Structure solution, refinement and modeling are accomplished using the Bruker SHELXTL package. The structure is solved by Patterson and Fourier methods and refined by full-matrix least-squares refinement on F$^2$. Allylic hydrogen atoms are found and refined from a Fourier difference map. The remaining hydrogens are fitted with a riding model. The final cycles of refinement converge with R=0.0369 and $R_w$=0.0857.

Synthesis of bis(diphenyl-bis(trimethylsilylimino) phosphorato)nickel (Formula 4)

The synthesis of the paramagnetic Formula 4 uses a modified procedure of the one reported by the Kuchen group. Dimethoxyethane nickel bromide (140 mg, 0.18 mmol) and [K][Ph$_2$P(=NTMS)$_2$] (54 mg, 0.36 mmol) are mixed in 3 ml of THF and stilted for 12 hours. The THF is evaporated from the resultant bright blue solution, and the residue is dissolved Into a 1:1 (v:v) hexane:toluene solvent. This solution is filtered through Celite, and the solvent evaporated in vacuo. The blue crystalline product (72 mg, 55%) is recrystallized from warm hexane. $^1$H NMR (300 MHZ, benzene-d$_6$, 298 K): δ −6.72 (bs, 8H, o-Ar), −0.29 (bs, 4H, p-Ar), 7.12 (bs, 8H, m-Ar), 13.91 (bs, 36H, SiCH$_3$).

Reaction of [Li][Ph$_2$P(=NTMS)2] and (DME)NiBr2:

Into 10 mL of ether ligand (Formula 3a) (300 mg, 0.832 mmol) is dissolved. The solution is cooled to −80° C. and 1 equivalent of BuLi (in hexanes) (2.61M, 0.319 mL, 0.832 mmol) is added and the solution is allowed to warm to 20° C. Meanwhile a dispersion of (DME)NiBr$_2$ (265 mg, 0.832 mmol) in 10 mL of ether is cooled to −80° C. The ligand solution is then transferred by cannula into the (DME)NiBr$_2$ dispersion, and the mixture warmed to 20° C. The solution turns deep blue and blue crystals begin to form. $^1$H NMR spectroscopy indicates that the principle product is Ph$_2$P (=NTMS)$_2$)$_2$Ni.

(Phenyl)(triphenylphosphine)(diphenyl-bis(trimethylsilylimino)phosphorato)-nickel (Formula 5)

[K][Ph$_2$P(=NTMS)$_2$] (1.06 grams, 2.53 mmol) in 5 mL of toluene is mixed with a dispersion of (PPh$_3$)$_2$Ni(Ph)Br (1.87 grams, 2.53 mmol) in 15 mL of toluene for 2 hours, the resulting deep red solution is filtered through Celite and solvent is reduced to about 13 mL in vacuo. Upon layering with hexane, the concentrate yields dark red cubic crystals (1.6 g, 83%). $^1$H NMR (300 MHz, benzene-d$_6$: 298 K): δ −0.29 (s, 18H, Si—CH$_3$), 6.48-6.53 (m, 3H, m/p-ArNi), 7.99-7.01 (m, 9H, m/p-PAr$_3$), δ −7.21-7.31 (m, 6H, m/p-Ar(PN$_2$)), 7.44-7.48 (m, 2H, o-ArNi), 7.84-7.90 (m, 6H, o-RAr$_3$), 8.16-8.22 (m, 4H, o-Ar(PN$_2$), $^3$P NMR (121.4 MHz, benzene-d$_6$, 298 K): δ 37.3 (s, 1P, PN$_2$), 29.2 (s, 1P, PPh$_3$). IR (KBr, cm$^{-1}$): 3031 (s), 2890 (s), 2878 (w), 2582 (w), 2316 (w), 1957 (s), 1887 (sh), 1668 (w), 1558 (s), 1434 (s), 1243 (s), 1083 (s), 831 (m). As calculated for C$_{42}$H$_{48}$N$_2$NiP$_2$Si$_2$: C, 66.58; H, 6.38. Found: C, 66.37; H, 6.21.

A red crystal of Formula 5 with dimensions 0.37×0.30× 0.24 mm is coated in PEK and mounted on a glass fiber which is placed under a stream of nitrogen on the goniometer head of a Bruker Apex CCD diffractometer. The full sphere of data is collected to 27.88° (θ) using graphite-monochromated MoK-α radiation (λ=0.71073 Angstroms) at 150 K. The reflections are collected using ω scans. A unit cell is collected in SMART and indexed in SAINT. The total number of reflections collected is 9250 between 1.74°-27.88° (θ). Structure solution, refinement and modeling are accomplished using the Bruker SHELXTL package. The structure is solved by direct methods and refined by full-matrix least-squares refinement on F$^2$. All hydrogens are fitted with a riding model. The final cycles of refinement converge with R=0.0331 and $R_w$=0.0539.

Synthesis of [(TMS2N)(Me)P(=NTMS)2]NiPh(PPh3) (Formula 6)

A solution of MeLi (5.2 mL, 1.6 M in diethyl ether, 8.3 mmol) is added to a solution of TMS$_2$NP(=NTMS)$_2$ (3.0 grams, 8.2 mmol) in diethyl ether (50 mL) at −78° C. The mixture is allowed to warm to room temperature and stirred for another 12 hours. The volatiles are removed in vacuo and a colorless solid of [Li][(TMS$_2$N)(Me)P(=NTMS)$_2$] is obtained and used for the next step without further purification.

[Li][(TMS$_2$N)(Me)P(=NTMS)$_2$] (1.80 grams, 4.65 mmol) in 15 mL of toluene is mixed with a dispersion of (PPh$_3$)$_2$Ni (Ph)Br (3.44 grams, 4.85 mmol) in 10 mL of toluene for 6 hours at room temperature. The resulting deep red solution is filtered through Celite and solvent is reduced to about 20 mL in vacuo. Upon layering with hexane (20 ml) and cooled to −28° C., a solid is obtained, which is mainly PPh$_3$. After removing all volatiles from the mother liquor and washing the residue with hexane, a yellow solid is obtained. (1.7 grams, 48%). $^1$H NMR (300 MHz, benzene-d$_6$, 298 K): δ −0.11 (s, 18H, NSiCH$_3$), 0.66 (s, 18H, N(SiCH$_3$)$_2$), 1.99 (d, j=12.9 Hz, 3H, PMe), 6.45 (s, 3H, m/p-ArNi). 6.93 (s, 2H, o-ArNi), 6.98 (s, 6H, p-PPh$_3$), 7.37 (s, 3H, o-PPh$_3$), 7.83 (s, 6H, o-PPh$_3$); $^{31}$P NMR (300 MHz, benzene-d$_6$, 298 K): δ 36.7 (s, $^1$P, PN$_2$), 32.0 (s, 1P, PPh$_3$), IR (Nujol, cm$^{-1}$): 1562 (m), 1287 (m), 1251 (s), 1115 (w), 1093 (m), 1075 (s), 1019 (w), 949 (s), 897 (m) 872 (w), 846 (s), 777 (w), 742 (w) 727 (m), 701 (m), 670 (w), 617 (w). As calculated for C$_{37}$H$_{59}$N$_3$NiP$_2$Si$_4$, C, 57.06; H, 7.64; N, 5.39. Found: C, 56.90; H, 7.25; N, 4.87.

Reaction of Formula 5 with Al(CH3)3:

In a 5 mm NMR tube, Formula 5 (11.5 mg, 15.2 μmol) is dissolved into 309 μL of benzene-d$_6$. In a separate vial, Al(CH$_3$)$_3$ (20 mg, 200 μmol) is dissolved into 1.05 mL of benzene-d$_6$. To the solution of Formula 5, 55 mg (1 equivalent) of the Al(CH$_3$)$_3$ solution is added. The solution turned black and Ni(0) precipitated. The $^1$H NMR spectrum of the products are consistent with a mixture of toluene and (Ph$_2$P (NTMS)$_2$)AlMe$_2$ an authentic sample of which is prepared as described below.

[N,N'-bis(trimethylsilyl)]-diphenyl-iminophosphonamidoaluminum dimethyl

The compound is synthesized by dissolving Formula 3a (0.673 grams, 1.87 mmol) in 3 mL of hexane and adding 1.5 equivalents of Al(CH$_3$)$_3$. Once the exothermic reaction is allowed to bubble and cool to 20° C., the solvent and residual Al(CH$_3$)$_3$ are removed by vacuum evaporation. Addition of about 0.4 mL of hexane and cooling to −30° C. for 12 hours yielded colorless crystals of Ph$_2$P(NTMS)$_2$AlMe$_2$ (700 mg, 90%) whose spectral data agreed with that repotted in the literature. $^1$H NMR (300 MHz, benzene-d$_6$, 298 K): δ −0.06 (s, 18H, Si—CH$_3$), −0.09 (s, 6H, AlCH$_3$), 7.71-7.81 (m, 4H, o-Ar), 6.99-7.12 (m, 6H, p/m-Ar). $^{31}$P NMR (121.4 MHz, benzene-d$_6$, 298 K): δ 30.49.

Polymerization Procedure:

Detailed procedures for the polymerization of ethylene using the catalyst disclosed would be known to those of skill in the art. Polymerizations are conducted in a 300 mL SS autoclave. The autoclave is dried in a 120° oven overnight and then brought directly into a glove-box and scrubbing agent (if used), catalyst (if not added by syringe), magnetic stir bar, and solvent are added.

The solvent toluene and monomer ethylene are purified as described elsewhere. The total impurity level in the reactor is determined by a saturating 100 mL of toluene with ethylene at 28 psig and 25° C. with stirring. After venting excess monomer inside a glove-box, titration of a 16 gram aliquot with 160 μL of a 21 mM standard solution of potassium and benzophenone in xylenes-tetraglyme gave a total Impurity level of 90 μM (expressed as [$H_2O$]).

Attempted Reactions of (Formula 2a-d) with Ethylene:

Into a 300 mL reaction vessel within a glovebox, Formula 2a and Formula 2b (200 mg, 400 μmol) and 100 mL of toluene are added to make a 4 mM solution. A magnetic stir bar is added to aid agitation. The reactor is sealed and removed from the glovebox. While stirring, 450 psig ethylene is added for 4 hours at 30° C. The same reaction is also performed at 70° C. No ethylene consumption is observed using a calibrated mass flow meter and no polymer is formed.

Screening of Formula 2c and Formula 2d are performed in the same manner and concentrations as described for Formulas 2a to 2b at 30° C. No ethylene consumption is detected and no polymer is formed.

In situ Generation of (Formulas 2a-b) in the Presence of ethylene

Comparative Example 1

Into a 300 ml reaction vessel within a glove-box, phosphorane (Formula 1) (111 mg, 400 μmol) and 100 mL of toluene are added to make a 4 mM solution. A magnetic stir bar is added to aid agitation. The reactor is sealed and removed from the glove-box. While stirring, 450 psig ethylene is added at 30° C. In a 25 ml stainless steel sample vessel are placed Ni($\eta^3$-($C_3H_5$))$_2$ (56 mg, 400 μmol) and 5 mL of toluene. The solution of Ni($\eta^3$($C_3H_5$)) is injected, and the reactor contents allowed to react at 17° C. The resulting solution is degassed and solvent evaporated. The polymer is washed with acidic methanol and dried in vacuum oven for 12 hours. This polymerization yielded 1.3 grams of polyethylene over 4 hours. The activity is calculated based on the dry mass of polymer. A $^{13}C$ NMR spectrum of this material is depicted in FIG. 6b.

Polymerization of ethylene with nickel(0) complexes and phosphorane (Formula 1)

Comparative Example 2

Ni(COD)$_2$ (55 mg, 200 μmol) and 45 mL of toluene are added into a 300 mL stainless steel autoclave, equipped with a glass insert, under nitrogen in a glove-box, to make a 4 mM solution. A magnetic stir bar is added for agitation. The autoclave is sealed and removed from the glove-box. While stirring, the vessel is pressurized with 30-300 psig of ethylene at 25° C. A solution of phosphorane (Formula 1) (73 mg, 200 μmol) in 5 mL of toluene is added via syringe (30 psig) or via over-pressurized 25 mL sample cylinder (300 psig). The mixture is stirred under ethylene at 25° C. for various times (Table 1). After venting the autoclave, the resulting solution is evaporated in vacuo. Polymer is washed with acidic methanol and dried in a vacuum oven for 12 hours. A representative $^{13}C$ NMR spectrum of these materials is presented in FIG. 6c.

Activation of Ni Complexes with PMAO:

A solution of the Ni complex (Formulas 2a to 2d), formula 4 or Formula 5, in 100 mL toluene, 0.1 mM and PMAO (0.02 M) is prepared and transferred to a 300 mL autoclave fitted with a glass insert in the glove-box. The autoclave is sealed, connected to a gas-manifold, briefly evacuated and then refilled with ethylene at 150 psig and 25° C. Rapid monomer consumption is noted using a calibrated mass flow meter (corresponding A>10$^6$ g $C_2H_4$/mol Ni×h) and a significant exotherm (>10° C.) generally ensued. After 1 hour, the autoclave is vented to atmosphere, and an aliquot of the clear, orange solution removed and filtered through a short plug of silica to remove catalyst and aluminoxane, washing with toluene. Analysis of the eluant by GC reveals the presence of dissolved ethylene and a mixture of 1- and 2-butenes.

Reaction of (Formula 5) with B($C_6F_5$)$_3$ and ethylene:

Into a 300 mL reaction vessel within a glove-box, Formula 5 (165 mg, 200 μmol) and 10 mL of toluene are added to make a 23 mM solution. A magnetic stir bar is added to aid agitation. In a Teflon cup is placed B($C_6F_5$)$_3$ (104 mg, 200 μmol) and which is wired to the thermo-well of the autoclave. The reactor is sealed and removed from the glove-box. While stirring, 300 psig (approximately 0.2 M) of ethylene is added at 30° C. Addition of borane is preformed by inverting the sealed reactor (and thus the Teflon cup containing B($C_6F_5$)$_3$) and the contents are allowed to react at 30° C. for 0.75 hours. The soluble material is analyzed by GC-MS after passing through a short plug of silica to remove catalyst. Activity is calculated based on total integral of mass flow curve vs. time. 1- and 2-butene are produced but no polymer is formed.

Reaction of (Formula 5) with Ni(COD)$_2$ and ethylene:

This reaction is performed in the same manner as above using: Ni(COD)$_2$ instead of B($C_6F_5$)$_3$. No ethylene consumption is observed and no polymer is formed.

Reaction of (Formula 5) with Rh(acac)($C_2H_4$)$_2$ and ethylene:

Twenty mg (77 μmol) of Rh(acac)($C_2H_4$)$_2$, a magnetic stir bar, and 0.95 mL of benzene-d$_6$ are added to a vial. After dissolution, 30 mg (40 μmol) of (Formula 5) is added and dissolved over 8 minutes. Thereafter 150 psig ethylene is added for 1 hour inside a 300 mL autoclave at 20° C. The solution is degassed and transferred to a 5 mm NMR tube. $^1H$ and $^{31}P$ NMR spectra are subsequently recorded. Activity of polymerization is based on integrated mass of polymer as determined from the $^1H$ NMR spectrum.

Polymerization of $C_2H_4$ with Complex (Formula 6):

A 300 mL reaction vessel is charged with 100 ml of toluene and a magnetic stir within a glovebox. In a Teflon cup, wired to the thermocouple well, is placed Formula 6 (155 mg, 200 μmol) (see FIG. 18 for an additional reference to this structure). The reactor is sealed and removed from the glovebox. While stirring, the solution is saturated at 25° C. with 290 psig ethylene (final [$C_2H_4$]=0.2 M). Addition of the complex is performed by inverting the Teflon cup, and the mixture is allowed to react 10 hours. The vessel is vented and the solution filtered through a basic Al$_2$O$_3$ column washing with hexane. All volatiles are removed in vacuum and an oligomeric PE is obtained. Yield: 4 mg. A $^1H$ NMR spectrum of this material is depicted in FIG. 5b and is consistent with presence of branching as revealed by an intense signal at δ 0.86 due to terminal methyl groups and very weak signals due to unsaturated end-groups at δ 4.95 (PE-CH=CH$_2$), 5.36 (PE-CH=CH-PE) and 5.80 (PE-CH=CH$_2$).

Polymerization of $C_2H_4$ with Complex (Formula 6) in the presence of Ni(COD)$_2$:

Into a 300 mL reaction vessel within a glove-box, Ni(COD)$_2$ (0.55 mg, 2 mmol) and 100 mL of toluene are added. A magnetic stir bar is added to aid agitation. In a internal Teflon cup is placed Formula 6 (155 mg, 200 μmol). The reactor is sealed and removed from the glove-box. While stirring, the solution is saturated at 25° C. with 290 psig ethylene (final [$C_2H_4$]=0.2 M). Addition of the complex is performed by inverting the Teflon cup, and the mixture is allowed to react 10 hours. The vessel is vented and the solution filtered through a basic $Al_2O_3$ column washing with hexane. All volatiles are removed in vacuum and a polymer is obtained: 85 mg.

A $^1$H NMR spectrum of this material is depicted in FIG. 5c. By comparison of FIGS. 5b and 5c with 5a it can be seen that the molecular weight of the material formed using Formula 6, either in the presence or absence of $Ni(COD)_2$, is considerably higher than that formed using $Ph_2P(NTMS)_2NiPh$ ($PPh_3$) in the presence of Rh(I). A $^{13}$C NMR spectrum of this material is depicted in FIG. 6a where aside from the difference in solvent employed, the structure of the branches present is essentially similar to that depicted in FIGS. 6b and 6c.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A method of polymerizing ethylene to form polyethylene, the method comprising the steps of:
   (a) combining at least one ethylene monomer and at least one nickel catalyst selected from the following formulas:

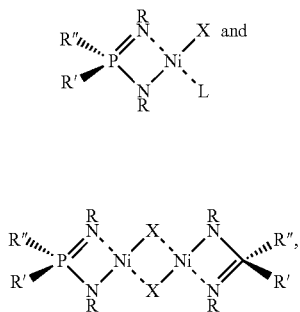

wherein R, R' and R" are independently selected from a $C_1$ to $C_{20}$ alkyl group, a $C_6$ to $C_{10}$ aryl group, a substituted $C_6$ to $C_{10}$ aryl group, and $NR'''_2$ where at least one of R' and R" is $NR'''_2$, wherein R''' is independently selected from a $C_1$ to $C_{20}$ alkyl group, a $C_6$ to $C_{10}$ aryl group, a substituted $C_6$ to $C_{10}$ aryl group, and $SiR'_3$; X is selected from a $C_1$ to $C_{20}$ alkyl group, a $C_6$ to $C_{10}$ aryl group, and a substituted $C_6$ to $C_{10}$ aryl group; and L is selected from a tertiary phosphine, a tertiary amine, nitrile, dialkyl sulfide, alkylaryl sulfide, and diaryl sulfide; or L and X together constitute a $\eta^3$-benzyl or substituted $\eta^3$-benzyl; and
   (b) polymerizing the mixture of Step (a) to yield at least one polyethylene polymer.

2. The method of claim 1, wherein L and X together constitute an $\eta^3$-benzyl or substituted $\eta^3$-benzyl.

3. The method of claim 1, wherein the two R groups join together to form a macrocyclic ring where a 1,n-alkylene, 1,4-phenylene moiety, or combinations thereof, are components of the ring such that the ring extends above and/or below the plane of the nickel, the nitrogen groups and phosphorus.

4. The method of claim 1, wherein R' and R" join together to form a ring.

5. The method of claim 4, wherein the ring consists of from 4 to 8 atoms and P, and wherein the ring can be substituted by one or two 1,2-phenylene moieties or substituted versions thereof.

6. The method of claim 1, where R" is $NR'''_2$.

7. The method of claim 1, where L is a tertiary phosphine.

8. The method of claim 1, further comprising the addition of an activator wherein the activator is selected from alkylaluminum, Lewis acidic triorganoborane, tertiary amine N-oxide, Rh(I) complex and Ni(0) complex.

9. The method of claim 8, wherein the Lewis acidic triorganoborane is $B(C_6F_5)_3$.

10. The method of claim 8, wherein the Rh(I) complex is $Rh(acac)(C_2H_4)_2$.

11. The method of claim 8, wherein the Ni(0) complex is $Ni(COD)_2$.

12. A method of polymerizing ethylene to form polyethylene, the method comprising the steps of:
   (i) combining at least one of $Rh(acac)(C_2H_4)_2$ or $Ni(COD)_2$ with at least one nickel catalyst according to the following formula:

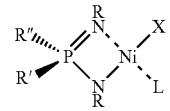

where R, R' and R" are independently selected from a $C_1$ to $C_{20}$ alkyl group, a $C_6$ to $C_{10}$ aryl group, a substituted $C_6$ to $C_{10}$ aryl group, and $NR'''_2$ where at least one of R' and R" is $NR'''_2$, wherein R''' is independently selected from a $C_1$ to $C_{20}$ alkyl group, a $C_6$ to $C_{10}$ aryl group, a substituted $C_6$ to $C_{10}$ aryl group, and $SiR'_3$; X is selected from a $C_1$ to $C_{20}$ alkyl group, a $C_6$ to $C_{10}$ aryl group, and a substituted $C_6$ to $C_{10}$ aryl group; and L is selected from a tertiary phosphine, dialkyl sulfide, alkylaryl sulfide, and diaryl sulfide, or L and X together constitute a $\eta^3$-benzyl or substituted $\eta^3$-benzyl;
   (ii) adding at least one ethylene monomer to the mixture formed in step (i); and
   (iii) polymerizing the mixture of step (ii) to yield at least one polyethylene polymer.

13. The method of claim 12, where R" is $NR'''_2$.

14. The method of claim 12, where L is a tertiary phosphine.

15. The method of claim 12, wherein the polyethylene polymer is branched polyethylene where the branches are predominantly equal to or greater than 6 carbon atoms in length.

16. A catalyst for use in the polymerization of ethylene, the catalyst comprising a compound according to following formula:

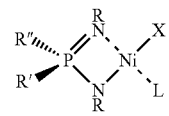

wherein R, R' and R" are independently selected from a $C_1$ to $C_{20}$ alkyl group, a $C_6$ to $C_{10}$ aryl group, a substituted $C_6$ to $C_{10}$ aryl group, and $NR'''_2$ where at least one of R' and R" is $NR'''_2$, wherein R''' is independently selected from a $C_1$ to $C_{20}$ alkyl group, a $C_6$ to $C_{10}$ aryl group, a substituted $C_6$ to $C_{10}$ aryl group, and $SiR'_3$; X is selected from a $C_1$ to $C_{20}$ alkyl group, a $C_6$ to $C_{10}$ aryl group, and a substituted $C_6$ to $C_{10}$ aryl group; and L is selected from a tertiary phosphine, dialkyl sulfide, alkylaryl sulfide, and diaryl sulfide, or L and X together constitute a $\eta^3$-benzyl or substituted $\eta^3$-benzyl.

17. The catalyst of claim 16, where R" is NR'''$_2$.

18. The catalyst of claim 16, where L is a tertiary phosphine.

* * * * *